US011524783B2

(12) United States Patent
Hack et al.

(10) Patent No.: US 11,524,783 B2
(45) Date of Patent: Dec. 13, 2022

(54) METHOD FOR DISINFECTING AN AIRCRAFT CABIN USING A LIGHTING ASSEMBLY AND A LIGHTING ASSEMBLY THEREFOR

(71) Applicant: BOMBARDIER INC., Dorval (CA)

(72) Inventors: Jonathan Wayne Hack, Burlington (CA); Robert C. Grant, Toronto (CA)

(73) Assignee: BOMBARDIER INC., Dorval (CA)

( * ) Notice: Subject to any disclaimer, the term of this patent is extended or adjusted under 35 U.S.C. 154(b) by 327 days.

(21) Appl. No.: 16/753,367

(22) PCT Filed: Oct. 3, 2018

(86) PCT No.: PCT/CA2018/051247
§ 371 (c)(1),
(2) Date: Apr. 3, 2020

(87) PCT Pub. No.: WO2019/068189
PCT Pub. Date: Apr. 11, 2019

(65) Prior Publication Data
US 2020/0331611 A1    Oct. 22, 2020

Related U.S. Application Data (60) Provisional application No. 62/568,989, filed on Oct. 6, 2017.

(51) Int. Cl.
*B64D 11/00*    (2006.01)
*B60Q 3/41*    (2017.01)
(Continued)

(52) U.S. Cl.
CPC ............... *B64D 11/00* (2013.01); *A61L 2/10* (2013.01); *B60Q 3/41* (2017.02); *B64D 47/02* (2013.01);
(Continued)

(58) Field of Classification Search
CPC ................... B64D 11/00; B64D 47/02; B64D 2011/0038; B60Q 3/41; A61L 2/10;
(Continued)

(56) References Cited

U.S. PATENT DOCUMENTS 8,999,238 B2    4/2015    Kreitenberg
9,149,549 B2    10/2015    Kreitenberg
(Continued)

FOREIGN PATENT DOCUMENTS

DE    102015207999    11/2016
EP    2668964    12/2013
(Continued)

OTHER PUBLICATIONS

International Searching Authority, Notification of Transmittal of the International Search Report and Written Opinion re: International Application No. PCT/CA2018/051247, dated Dec. 27, 2018.
(Continued)

*Primary Examiner* — Bao Q Truong
(74) *Attorney, Agent, or Firm* — Norton Rose Fulbright Canada LLP (57) ABSTRACT

A lighting assembly for an aircraft includes a visible light source generating visible light and an ultraviolet light source generating ultraviolet light. The visible light source is disposed adjacent to the ultraviolet light source. The visible light source illuminates a first illumination area with the visible light when the lighting assembly operates in a first operation mode. The ultraviolet light source illuminates a second illumination area with the ultraviolet light when the lighting assembly operates in a second mode of operation. The first illumination area substantially overlaps the second illumination area.

17 Claims, 7 Drawing Sheets

(51) Int. Cl.
*A61L 2/10* (2006.01)
*B64D 47/02* (2006.01)

(52) U.S. Cl.
CPC ....... *A61L 2202/14* (2013.01); *A61L 2202/25* (2013.01); *A61L 2209/111* (2013.01); *A61L 2209/12* (2013.01); *B64D 2011/0038* (2013.01)

(58) Field of Classification Search
CPC ............. A61L 2202/14; A61L 2202/25; A61L 2209/111; A61L 2209/12
See application file for complete search history.

(56) References Cited

U.S. PATENT DOCUMENTS

| | | | |
|---|---|---|---|
| 9,550,006 | B2 | 1/2017 | Boodaghians et al. |
| 9,623,133 | B2 | 4/2017 | Childress et al. |
| 2007/0053188 | A1* | 3/2007 | New ........................ B60Q 3/43 362/276 |
| 2012/0051977 | A1 | 3/2012 | Boodaghians et al. |
| 2012/0221192 | A1 | 8/2012 | Seibt |
| 2012/0273340 | A1 | 11/2012 | Felix |
| 2014/0059796 | A1 | 3/2014 | Boodaghians et al. |
| 2014/0241941 | A1 | 8/2014 | Kreitenberg |
| 2015/0064065 | A1 | 3/2015 | Kreitenberg |
| 2016/0271289 | A1 | 9/2016 | Duffy |
| 2016/0339133 | A1 | 11/2016 | Lichtblau |
| 2017/0035920 | A1* | 2/2017 | Boodaghians ......... B64D 11/00 |

FOREIGN PATENT DOCUMENTS

| | | |
|---|---|---|
| KR | 200400220 | 11/2005 |
| WO | 2017204774 | 11/2017 |

OTHER PUBLICATIONS

English translation of German patent document No. DE 102015207999 dated Nov. 3, 2016, https://patents.google.com/patent/DE102015207999A1/en?oq=DE102015207999, accessed on Jan. 16, 2020.

English translation of Korea patent document No. KR 200400220 dated Nov. 3, 2005, https://patents.google.com/patent/KR200400220Y1/en?oq=KR200400220, accessed on Jan. 16, 2020.

English translation of Europe patent document No. EP 2668964 dated Dec. 4, 2013, https://patents.google.com/patent/EP2668964A1/en?oq=EP2668964, accessed on Jan. 16, 2020.

* cited by examiner

Fig. 2

METHOD FOR DISINFECTING AN AIRCRAFT CABIN USING A LIGHTING ASSEMBLY AND A LIGHTING ASSEMBLY THEREFOR

CROSS-REFERENCE TO RELATED APPLICATION(S)

This application is a national phase application under 35 U.S.C. 371 of International Patent Application No. PCT/CA2018/051247 filed on Oct. 3, 2018, which claims priority from U.S. Provisional Patent Application Ser. No. 62/568,989 filed on Oct. 6, 2017, the entire content of which is incorporated herein by reference.

FIELD OF THE INVENTION

The present invention concerns a method for disinfecting a vehicle cabin using a lighting assembly. The present invention also provides a lighting assembly for disinfecting a vehicle cabin. The vehicle cabin may be an aircraft cabin, a train cabin, a boat cabin, or the like.

DESCRIPTION OF THE BACKGROUND AND RELATED ART

As should be apparent to those skilled in the art, the interior of a vehicle, such as an aircraft, experiences continuous use during its operational lifetime. This means that the vehicle receives thousands of passengers during its operational lifetime.

To keep the vehicle cabin clean, vehicle operators typically employ teams of workers to clean and sanitize the surfaces in the vehicle cabin.

In recent years, a desire has developed for improved methods and devices to assist with sanitizing and cleaning vehicle cabins.

This includes an increased desire to disinfect the surfaces in the vehicle cabin to reduce the potential for the spread of germs.

SUMMARY OF THE INVENTION

The present invention addresses one or more of the deficiencies with respect to the prior art.

In particular, the present invention provides a lighting assembly for an aircraft that includes a visible light source generating visible light and an ultraviolet light source generating ultraviolet light. The visible light source is disposed adjacent to the ultraviolet light source. The visible light source illuminates a first illumination area with the visible light when the lighting assembly operates in a first operation mode. The ultraviolet light source illuminates a second illumination area with the ultraviolet light when the lighting assembly operates in a second mode of operation. The first illumination area substantially overlaps the second illumination area.

It is contemplated that, in at least one embodiment, the visible light source and the ultraviolet light source are disposed on a single substrate.

The visible light source may encompass a plurality of visible light generators.

A further embodiment contemplates that the plurality of visible light generators are LEDs.

Still further, in one embodiment, the ultraviolet light source may include a plurality of ultraviolet light generators. The plurality of ultraviolet light generators may be LEDs.

A first number of the plurality of visible light generators is contemplated to be greater than or equal to a second number of the plurality of ultraviolet light generators.

The lighting assembly also may include a controller connected to the lighting assembly to control operation of the visible light source and the ultraviolet light source.

In addition, it is contemplated that the lighting assembly may have a first sensor connected to the controller to detect when a door to the aircraft is closed and generate a first input signal for the controller.

A second sensor may be provided to detect the absence of a person in the aircraft and generate a second input for the controller.

The second sensor may be a motion sensor.

In another contemplated embodiment, the controller may be operatively connected to a management system and receive a third input from the management system indicating that the aircraft is parked.

It is also contemplated that the controller may be connected to a plurality of window shades and close the window shades when the ultraviolet light source operates in the second mode of operation.

In addition, the controller may be connected to a plurality of seats and position the seats in a configuration so that the seats are bathed in the ultraviolet light when the ultraviolet light source operates in the second mode of operation.

The present invention also encompasses a method of operating a lighting assembly that includes a visible light source generating visible light, an ultraviolet light source generating ultraviolet light, a controller connected to the lighting assembly to control operation of the visible light source and the ultraviolet light source, a first sensor connected to the controller to detect when a door to the aircraft is closed and generate a first input, and a second sensor to detect the absence of a person in the aircraft and generate a second input, wherein the visible light source is disposed adjacent to the ultraviolet light source, wherein the visible light source illuminates a first illumination area with the visible light when the lighting assembly operates in a first operation mode, and wherein the ultraviolet light source illuminates a second illumination area with the ultraviolet light when the lighting assembly operates in a second mode of operation, and wherein the controller is operatively connected to a management system and receives a third input from the management system indicating that the aircraft is parked. The method includes receiving, by the controller, the first input, receiving, by the controller, the second input, receiving, by the controller, the third input, and initiating the second operation mode after receipt of the first input, the second input, and the third input.

It is contemplated that the controller also may be connected to a plurality of window shades. If so, the method also includes closing, by the controller, the window shades when the ultraviolet light source operates in the second mode of operation.

Still further, the controller may be connected to a plurality of seats.

If so, the method may position the seats in a configuration so that the seats are bathed in the ultraviolet light when the ultraviolet light source operates in the second mode of operation.

In addition, the method may include positioning the seats in a configuration so that the seats are bathed in the ultraviolet light when the ultraviolet light source operates in the second mode of operation.

The method is contemplated to include an operation for checking periodically, by the controller, the first input, the second input, and the third input.

Upon failure of receipt of at least one of the first input, the second input, or the third input the controller may stop the second operation mode.

Further aspects of the present invention will be made apparent from the paragraphs that follow.

BRIEF DESCRIPTION OF THE DRAWING(S)

The present invention will now be described in connection with the drawings appended hereto, in which.

DETAILED DESCRIPTION OF EMBODIMENT(S) OF THE INVENTION

The present invention will now be described in connection with one or more embodiments thereof. The discussion of the embodiments is not intended to be limiting of the present invention. To the contrary, any discussion of specific embodiments is intended to exemplify the breadth and scope of the present invention. As should be apparent to those skilled in the art, variations and equivalents of the embodiment(s) described herein may be employed without departing from the scope of the present invention. Those variations and equivalents are intended to be encompassed by the scope of the present patent application.

Figure 1:
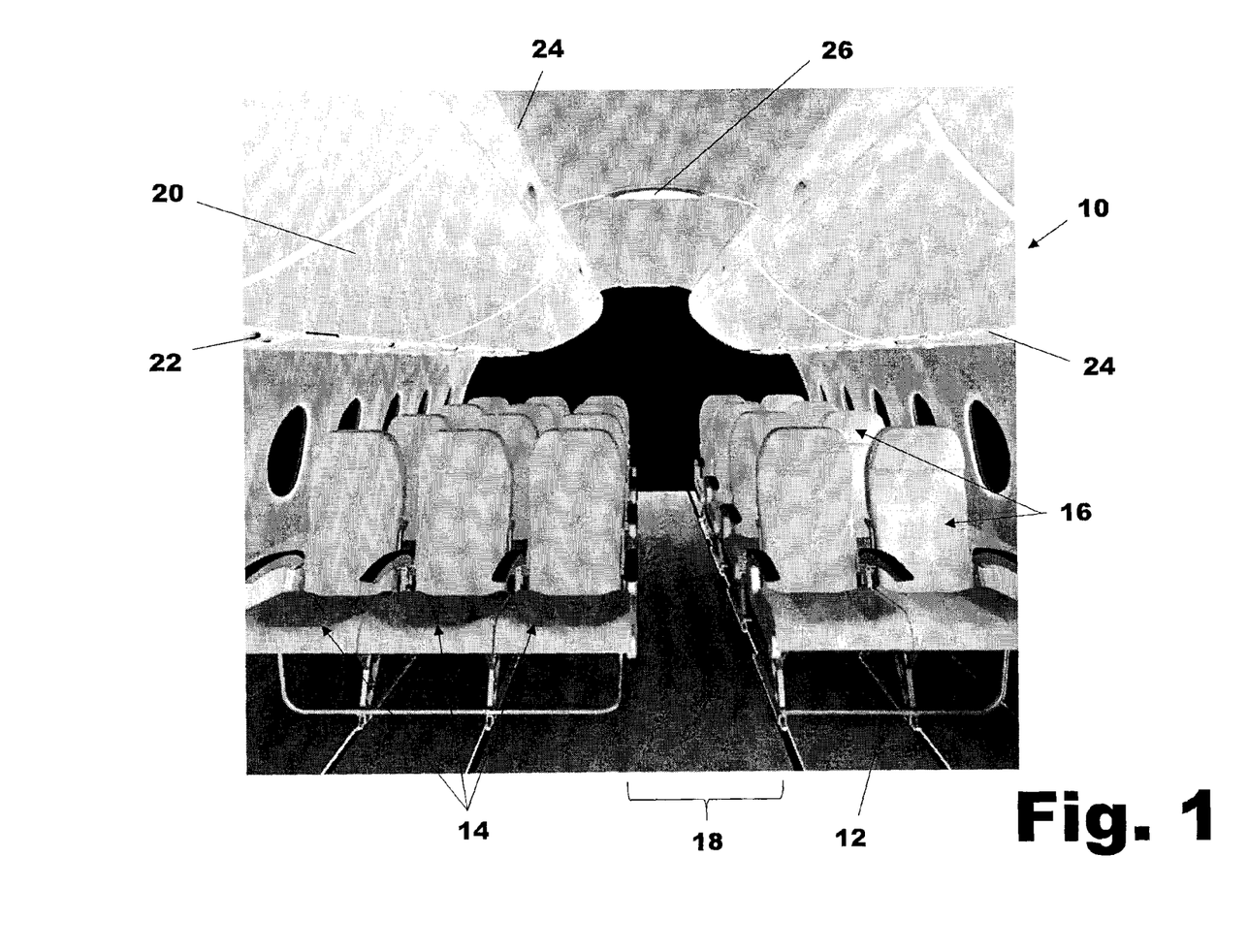
FIG. 1 is a perspective illustration of an interior of an aircraft cabin that incorporates the lighting assembly of the present invention.

FIG. 1 is a perspective illustration of the interior of an aircraft cabin 10. The aircraft cabin 10 includes a floor 12 supporting a plurality of seats 14 thereon. The seats 14 are arranged in rows 16, which are disposed astride a center aisle 18. As should be apparent to those skilled in the art, the aircraft cabin 10 may include any number of seats 14 in any arrangement for the transportation of passengers. Accordingly, the arrangement of seats 14 illustrated in FIG. 1 is intended to be illustrative of one possible arrangement of seats 14. FIG. 1 should not be understood to be limiting of the present invention. For example, the aircraft cabin 10 may include two or more aisles, etc.

It is noted that the configuration of the aircraft cabin 10 is considered typical for a commercial aircraft. While the discussion that follows generally encompasses features that are common to commercial aviation, the present invention is not limited to commercial aircraft. To the contrary, the present invention is intended to be employed in private aircraft, corporate aircraft, or the like.

Separately, while the present invention is described in connection with aircraft, the present invention may be employed in other vehicles including, but not limited to, boats, ships, train cars, metro cars, busses, etc.

The aircraft cabin 10 is provided with overhead storage compartments 20 that are disposed above the rows 16 of seats 14, on either side of the center aisle 18. The storage compartments 20 are provided to stow the belonging of passengers.

Passenger lighting assemblies 22 are disposed above the seats 14. The passenger lighting assemblies 22 include lights that may be activated by the passengers, typically via a switch located on the passenger lighting assembly 22 or on the armrest of the passenger's seat 14. The passenger lighting assembles 22 provide light concentrated at the passenger's seat 14 to provide illumination for the passenger in the seat 14.

The aircraft cabin 10 also includes cabin lighting assemblies 24 that are disposed along the length of the aircraft cabin 10, above and below the overhead storage compartments 20. The cabin lighting assemblies 24 provide light to the interior of the aircraft cabin 10. The cabin lighting assemblies 24 are contemplated to be the primary lighting sources within the aircraft cabin 10.

The aircraft cabin 10 also may include several other lighting assemblies 26. In the illustrated embodiment, the other lighting assemblies 26 are positioned on the ceiling of the aircraft cabin 10. The other lighting assemblies 26 provide light to various parts of the aircraft cabin 10, as required or as desired. It is noted that the other lighting assemblies 26 are intended to encompass any lighting assemblies 26 that are positioned anywhere in the aircraft cabin 10, such as in the galley, in the lavatory, on the flight deck, etc.

The passenger lighting assemblies 22, the cabin lighting assemblies 24, and the other lighting assemblies 26 are contemplated to be controlled by the cabin crew, typically through a control panel accessible from a crew area within the aircraft cabin 10. As noted, the passengers also have control over the passenger lighting assemblies 22. However, the crew is contemplated to be able to override any inputs provided by the passengers to the passenger lighting assemblies 22. In other words, the crew may enable and disable the operation of the passenger lighting assemblies from a central control location, selected details of which are provided below.

It is noted that the exact locations of the passenger lighting assemblies 22, the cabin lighting assemblies 24, and the other lighting assemblies 26 are merely illustrative of one possible configuration of these lighting assemblies 22, 24, 26. The lighting assemblies 22, 24, 26 may be disposed at other locations within the aircraft cabin 10 without departing from the scope of the present invention. Moreover, the present invention should not be understood to be limited to the number of lighting assemblies 22, 24, 26 that are described and/or illustrated herein.

Figure 2:
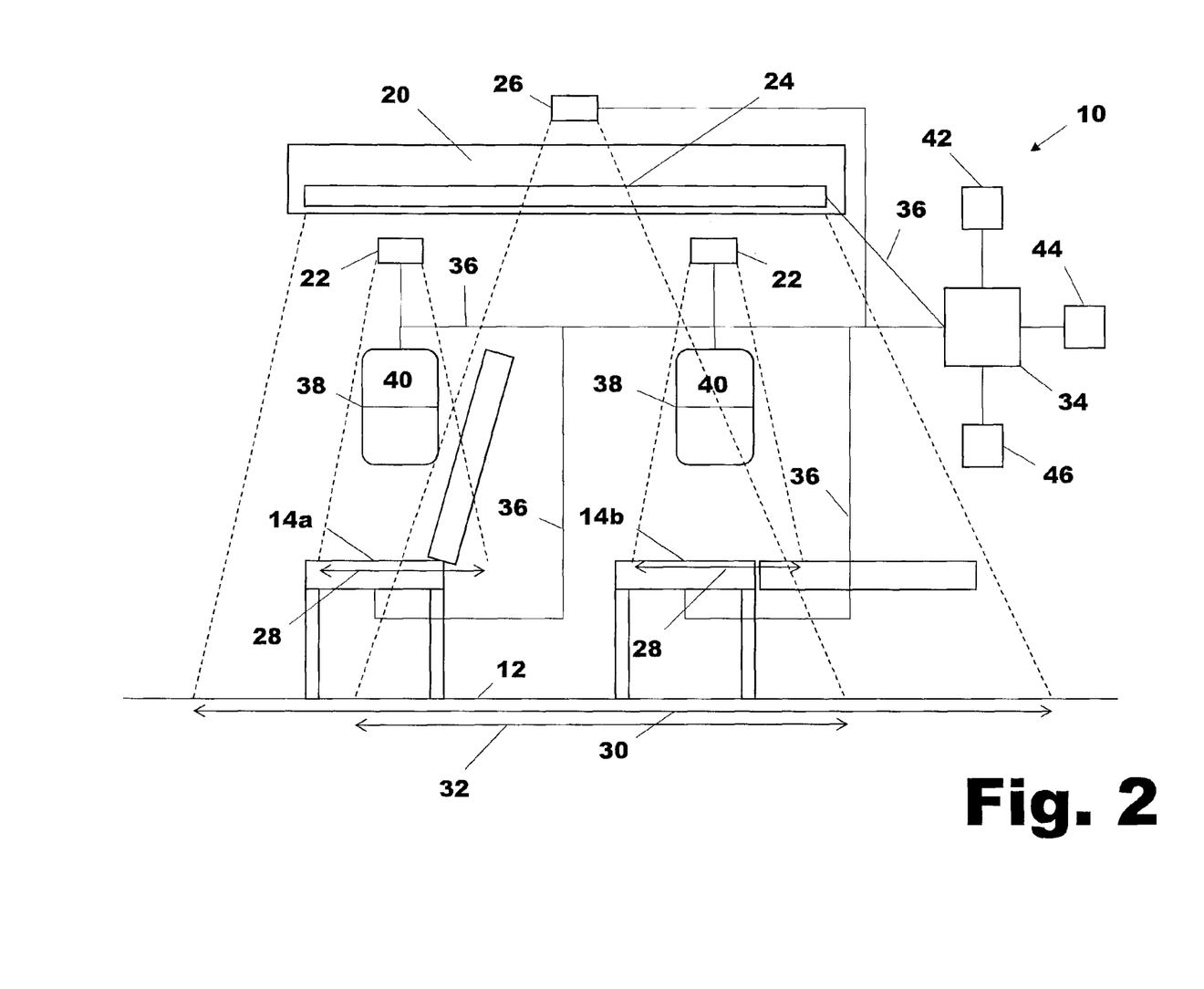
FIG. 2 is a graphical side view of a portion of the aircraft cabin illustrated in FIG. 1.

FIG. 2 is a graphical side view of the aircraft cabin 10, providing a graphical representation of additional aspects of the present invention. In particular, FIG. 2 illustrates two seats 14a, 14b representing two rows 16 in the aircraft cabin 10. The seats 14a, 14b are connected to the floor 12 of the aircraft cabin 10 via tracks, which are located in the floor.

In FIG. 2, the seats 14a, 14b are illustrated as graphical representations of individual ones of the seats 14 shown in FIG. 1. The seats 14a, 14b are contemplated to be identical to one another in construction. However, the seats 14a, 14b need not be identical to practice the present invention.

The seat 14a is illustrated in an upright position. The upright position also is referred to as the "TTL position," which refers to the position of the seat 14 during Taxi, Take-off, and Landing. The seat 14b is in a fully reclined position. The seats 14 in the aircraft cabin 10 may be positioned in any of a number of configurations, as should be apparent to those skilled in the art.

FIG. 2 also illustrates two passenger lighting assemblies 22, one disposed above the seat 14a and the other disposed above the seat 14b. In addition, a cabin lighting assembly 24 is illustrated above both seats 14a, 14b. Still further, FIG. 2 depicts one of the other lighting assemblies 26, which is contemplated to be disposed on the ceiling of the aircraft cabin 10.

Each of the passenger lighting assemblies 22 generates light that illuminates a first illumination area 28. Since FIG. 2 is a side view of the aircraft cabin 10, only the lengths of two of the first illumination areas 28 are designated. As should be apparent to those skilled in the art, each the first illumination areas 28 also has a width that is transverse to the length of the illumination area 28.

The length of the first illumination area 28 extends along a longitudinal direction of the aircraft cabin 10. The width of the first illumination area 28, therefore, extends in a lateral direction of the aircraft cabin 10. For clarity, in FIG. 2, the longitudinal direction of the aircraft cabin 10 is illustrated. The longitudinal direction of the aircraft is consistent with the travel direction of the aircraft. Furthermore, the seats 14a, 14b are facing toward the front of the aircraft cabin 10 and, accordingly, are positioned to face the direction of travel of the aircraft. It is noted that this orientation is merely illustrative and, therefore, not intended to be limiting of the present invention.

One overhead lighting assembly 24 is illustrated in FIG. 2. The illustrated overhead lighting assembly 24 extends under the overhead storage compartments 20. While not illustrated, a separate overhead lighting assembly 24 typically extends above the storage compartments 20.

The overhead lighting assembly 24 is contemplated to be a continuous lighting assembly that extends along the length of the aircraft cabin 10. The overhead lighting assembly 24 generates light that illuminates a second illumination area 30.

One other lighting assembly 26 is illustrated in FIG. 2. As noted above, and as illustrated in FIG. 1, the other lighting assembly 26 is contemplated to be mounted on the ceiling of the aircraft cabin 10. The other lighting assembly 26 generates light that illuminates a third illumination area 32.

As should be apparent from FIG. 2, the passenger lighting assembly 22, the overhead lighting assembly 24, and the other lighting assembly 26 are disposed in the aircraft cabin 10 so that the first lighting area 28, the second lighting area 30, and the third lighting area 32 substantially overlap one another. As a result, the passenger lighting assembly 22, the overhead lighting assembly 24, and the other lighting assembly 26 are positioned so that light generated by the lighting assemblies illuminates most, if not all, of the surfaces within the aircraft cabin 10.

With respect to "substantial overlap" between first lighting area 28, the second lighting area 30, and/or the third lighting area 32, it is contemplated that areas not receiving light generated by the lighting assemblies will be less than 20% of the total area of the surfaces within the aircraft cabin. In other words, it is contemplated that the light generated by the lighting assemblies will reach 80% or more of the total area of the surfaces within the aircraft cabin 10, including both direct and indirect lighting. The present invention, however, is not intended to be limited to a substantial overlap of greater than or equal to 80%. To the contrary, the present invention also is intended to encompass a substantial overlap of greater than or equal to 85%, 90%, 95%, 97%, and/or 100%.

It is noted that the passenger lighting assembly 22, the overhead lighting assembly 24, and the other lighting assembly 26 are not intended to be the only lighting assemblies that are disposed in the aircraft cabin 10. As noted above, it is contemplated that the aircraft cabin 10 may include any number of other lighting assemblies 26 at any other location, as required and/or desired. For example, it is contemplated that other lighting assemblies 26 will be positioned in the lavatory, in the galley, and on the flight deck of the aircraft. The other lighting assemblies 26 may be positioned at still further locations, as should be apparent to those skilled in the art.

A controller 34 is provided in the aircraft cabin 10 to control the operation of the passenger lighting assemblies 22, the overhead lighting assemblies 24, and the other lighting assemblies 26. The controller 34 is contemplated to connect to the passenger lighting assemblies 22, the overhead lighting assemblies 24, and the other lighting assemblies 26 via one or more communication lines 36. The communication lines 36 are intended to be illustrative of a common data bus, wire, wires, optical fibers, wireless connections, or the like, that may be used alone or together to operatively connect the various components within the aircraft cabin 10 to one another. As such, the communication lines 36 are illustrative of connections generally and not intended to imply or suggest any one particular embodiment that may be considered as limiting of the present invention.

The controller 34 also is connected to the windows 38 in the aircraft cabin 10. In particular, the controller 34 is contemplated to control the window shades 40. The window shades 40 may be mechanically raised and lowered, such as may be applied to a solid plastic shade or a pleated fabric shade, for example. Still further, the window shades 40 may electrochromic, meaning that the opacity of the window shades 40 may be controlled depending upon the type of signal transmitted via the communication lines 36 to the window shades 40.

FIG. 2 also shows that the controller 34 is operatively connected to a management system 42, a first sensor 44, and a second sensor 46, the details of which are discussed in greater detail below.

As discussed in connection with FIGS. 3-6, each of the lighting assemblies 22, 24, 26 are contemplated to incorporate a visible light source 48 and an ultraviolet light source 50.

Figure 3:
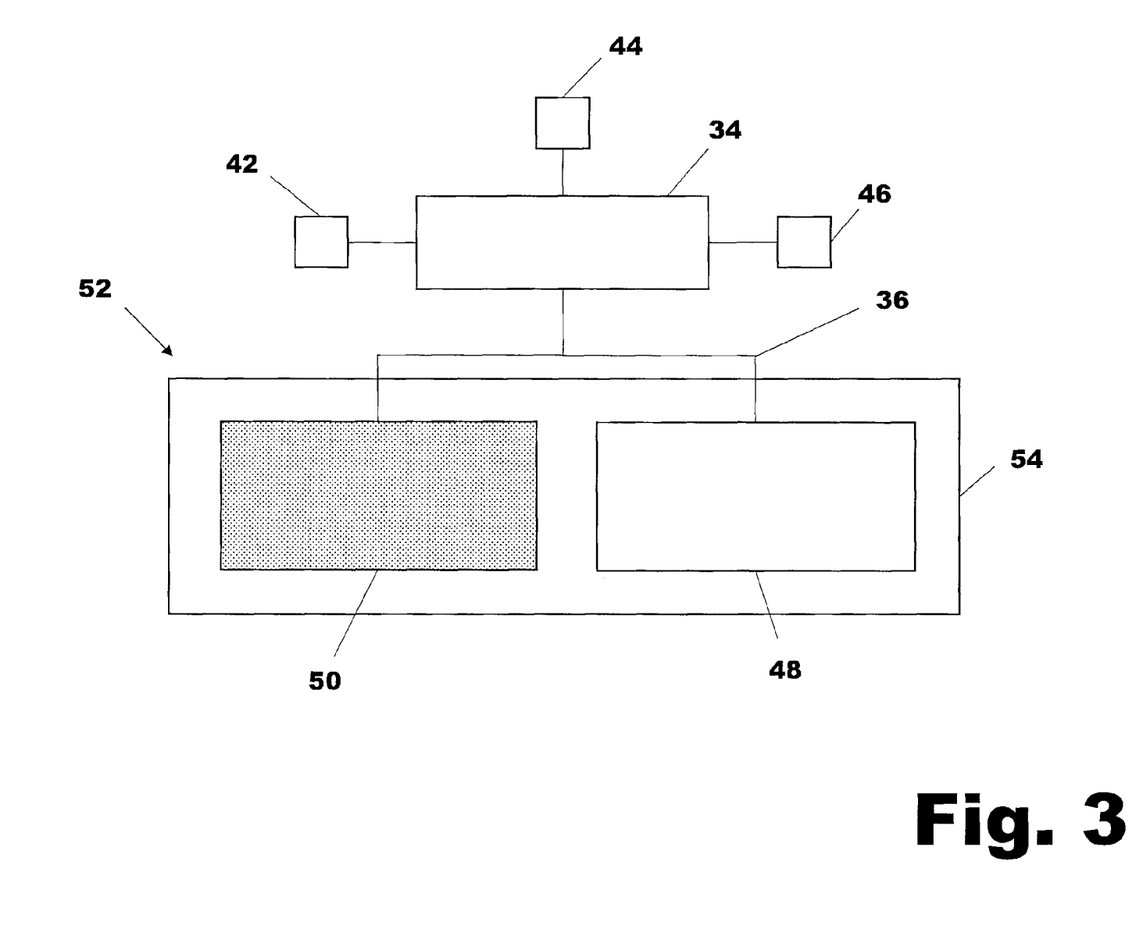
FIG. 3 is a graphical representation of a first contemplated embodiment of a lighting assembly according to the present invention.

FIG. 3 illustrates a first embodiment of a lighting assembly 52 according to the present invention. The lighting assembly 52 includes a visible light source 48 and an ultraviolet light source 50, which are disposed on a substrate 54.

The visible light source 48 and the ultraviolet light source 50 are contemplated to be light emitting diodes ("LEDs"). However, any other light emitting devices may be employed without departing from the scope of the present invention. For example, the two light sources 48, 50 may be incandescent, halogen, fluorescent, or the like, including combinations thereof.

The visible light source 48 emits visible light. Visible light encompasses light that is detectable by the human eye. Visible light includes, but is not limited to, light with a wavelength in a range from 390 to 700 nm.

The ultraviolet light source 50 emits ultraviolet light. Ultraviolet light encompasses light that is not detectible, for the most part, by the human eye. Ultraviolet light includes, but is not limited to, light with a wavelength in a range from about 10 to 400 nm.

As should be apparent to those skilled in the art, ultraviolet light possesses anti-bacterial and anti-viral properties. In other words, ultraviolet light is effective in disinfecting surfaces exposed thereto. For this reason, ultraviolet light is employed in many contexts as part of a cleaning and/or sterilization regimen.

The present invention provides a lighting assembly 22, 24, 26 that incorporates both a visible light source 48 and an ultraviolet light source 50. The visible light source 48 is contemplated to be disposed adjacent to the ultraviolet light source 50, preferably on the same substrate 54. The visible light source 48 is contemplated to illuminate the illumination areas 28, 30, 32 that are associated with the lighting assemblies 22, 24, 26. Being disposed adjacent to the visible light source 48, the ultraviolet light source 50 also is contemplated to substantially overlap and, therefore, illuminate the same illumination areas 28, 30, 32. In other words, both the visible light source 48 and the ultraviolet light source 50 are contemplated to substantially overlap and, therefore, illuminate the same illumination areas 28, 30, 32. As such, in the illustrated embodiment of the present invention, the illumination areas 28, 30, 32 for the visible light and for the ultraviolet light are shown as being identical. However, as discussed above, it should be understood that the illumination areas 28, 30, 32 for the visible light may differ from those for the ultraviolet light without departing from the scope of the present invention. As defined herein, the illumination areas 28, 30, 32 for the visible light is contemplated to substantially overlap the same illumination areas for the ultraviolet light. Since the visible light source 48 is contemplated to be disposed adjacent to the ultraviolet light source 50 on the same substrate 54, for example, the substantial overlap is contemplated to be greater than or equal to at least one of 90%, 95%, 97%, 99%, or 100%.

The lighting assemblies 22, 24, 26 are contemplated to operate in two modes of operation. In a first mode of operation, the lighting assemblies 22, 24, 26 are contemplated to emit the visible light. As such, this first mode of operation also is referred to as a visible light operation mode. In a second mode of operation, the lighting assemblies 22, 24, 26 are contemplated to emit the ultraviolet light. This second mode of operation, therefore, also is referred to as an ultraviolet mode of operation. The controller 34 controls the lighting assemblies 22, 24, 26 so that they operate in either one or both of the first mode of operation and the second mode of operation.

It is noted that, in the second mode of operation, where the ultraviolet light is emitted by the lighting assemblies 22, 24, 26, visible light also may be emitted. In the first mode of operation, by contrast, the lighting assemblies 22, 24, 26 are contemplated to emit only visible light.

When in the first mode of operation, to the extent that the lighting assemblies 22, 24, 26 emit ultraviolet light, any such ultraviolet light is contemplated to be of a modest intensity, within a light intensity range considered normal for ambient, environmental light. In other words, if ultraviolet light is emitted in the first mode of operation, the ultraviolet light is contemplated to fall within acceptable intensity limits for any other ambient lighting conditions, such as those experienced in an environment with fluorescent light, for example.

As noted above, it is contemplated that the visible light source 48 and the ultraviolet light source 50 will be LEDs that are disposed on the same substrate 54, such as a printed circuit board or the like.

For the lighting assembly 52 illustrated in FIG. 3, there is one visible light source 48 and one ultraviolet light source 50. However, this is not the only arrangement of visible light sources 48 and ultraviolet light sources 50 that are contemplated to fall within the scope of the present invention.

Figure 4:
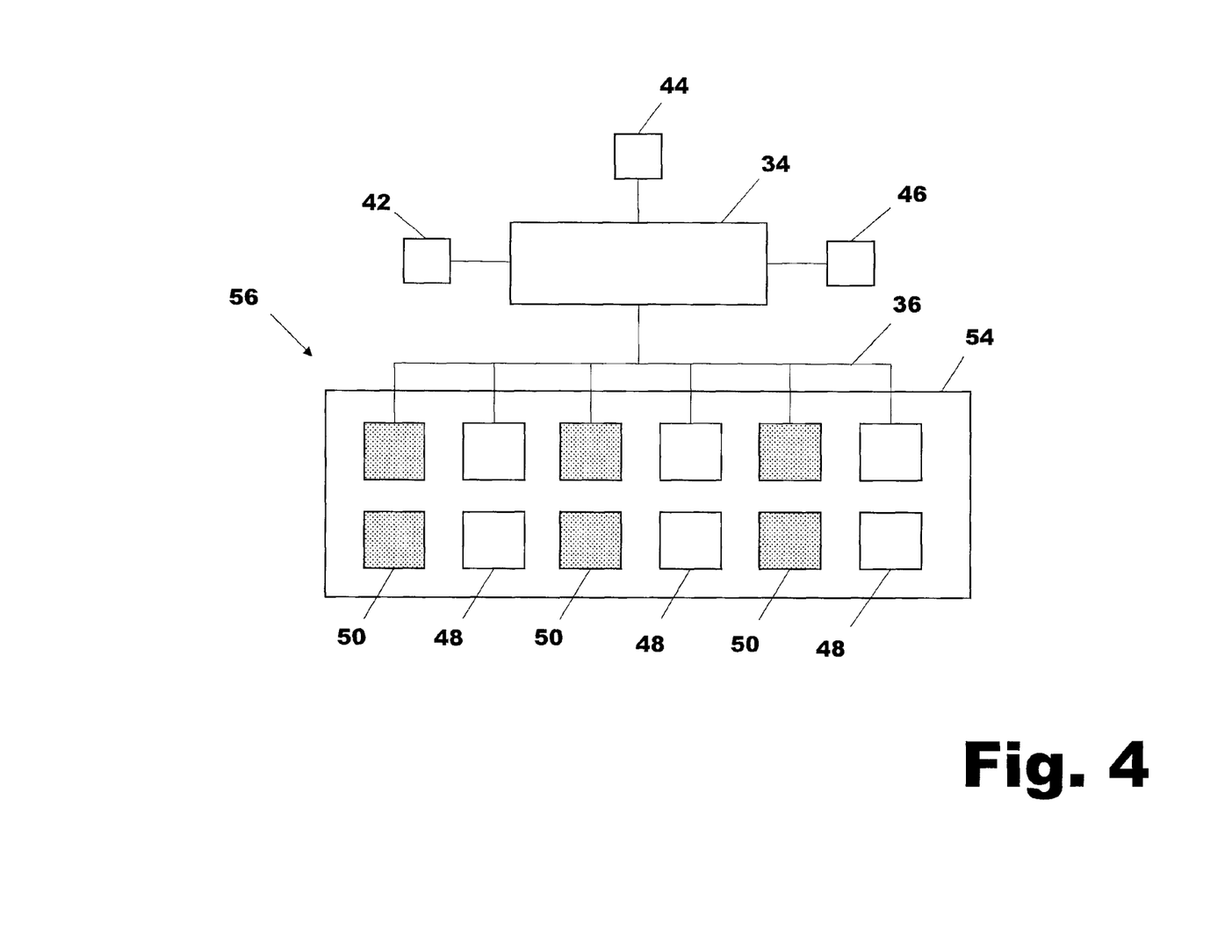
FIG. 4 is a graphical representation of a second contemplated embodiment of a lighting assembly according to the present invention.

FIG. 4 illustrates a second embodiment of a lighting assembly 56 according to the present invention. The lighting assembly 56 incorporates a plurality of visible light sources 48 and a plurality of ultraviolet light sources 50 on the substrate 54. As illustrated in FIG. 4, the visible light sources 48 and ultraviolet light sources 50 are arranged in columns on the substrate 54.

Figure 5:
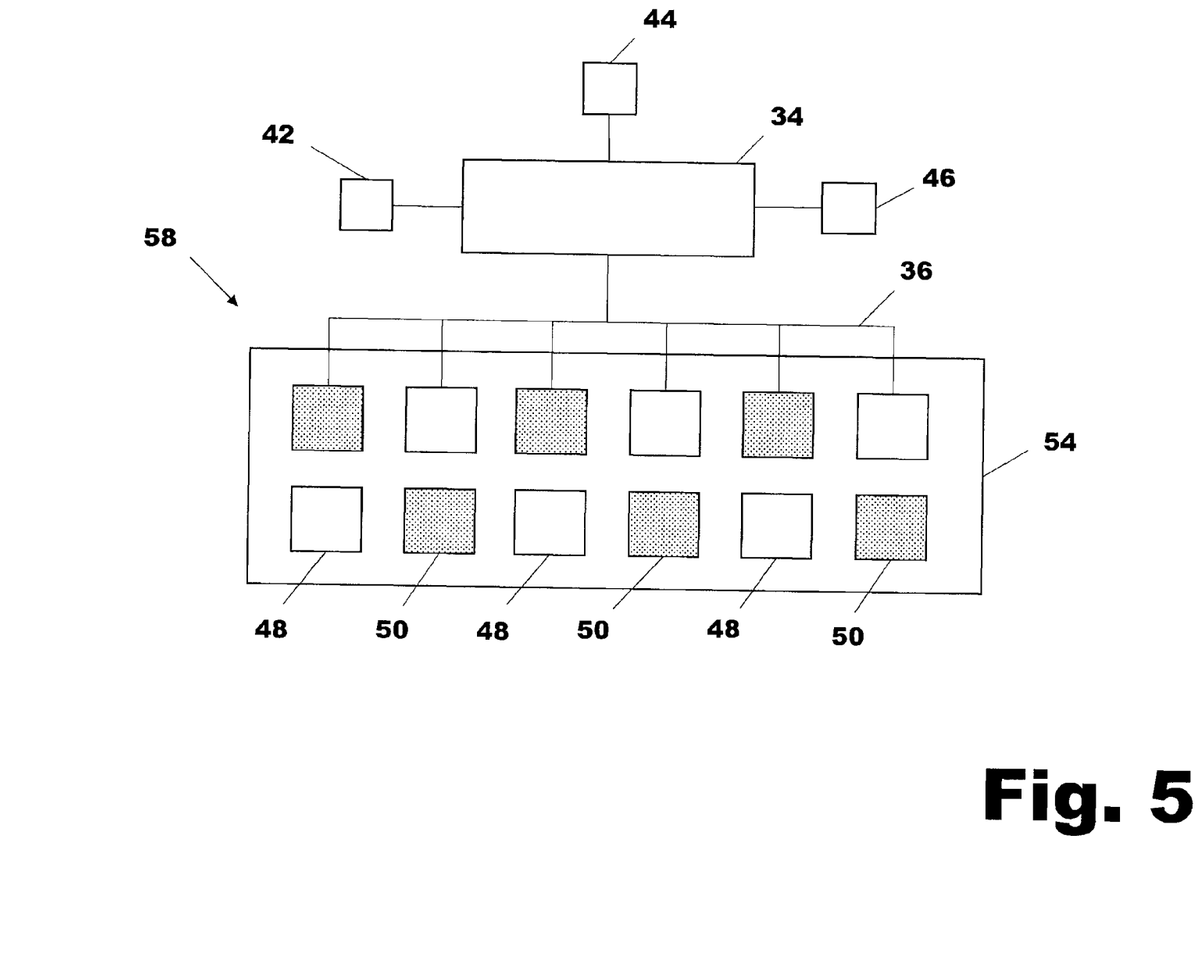
FIG. 5 is a graphical representation of a third contemplated embodiment of a lighting assembly according to the present invention.

FIG. 5 illustrates a third embodiment of a lighting assembly 58 according to the present invention. The lighting assembly 58 also incorporates a plurality of visible light sources 48 and a plurality of ultraviolet light sources 50 on the substrate 54. However, for this lighting assembly 58, the light sources 48, 50 are disposed in an alternating pattern, like a checkerboard.

Figure 6:
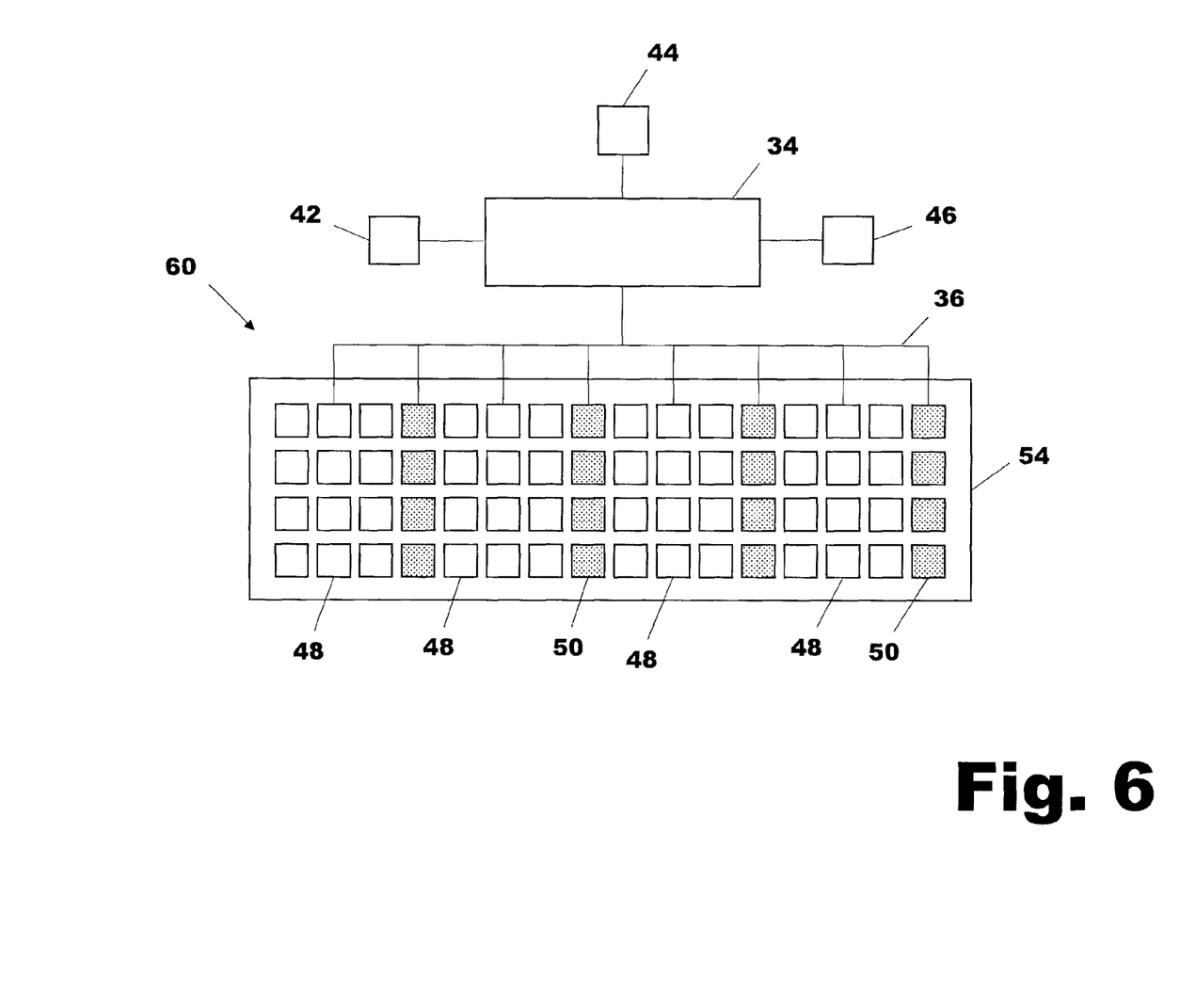
FIG. 6 is a graphical representation of a fourth contemplated embodiment of a lighting assembly according to the present invention.

FIG. 6 illustrates a fourth embodiment of a lighting assembly 60 according to the present invention. The lighting assembly 60 includes a plurality of visible light sources 48 and a plurality of ultraviolet light sources 50 on the substrate 54. As in the second embodiment, the visible light sources 48 and the ultraviolet light sources 50 are arranged in columnar fashion on the substrate 54. However, for this fourth embodiment, the lighting assembly 60 includes a greater number of visible light sources 48 than ultraviolet light sources 50.

As noted above, the visible light sources 48 and the ultraviolet light sources 50 are contemplated to be LEDs. With a greater number of visible light sources 48 on the substrate 54, it is contemplated that the lighting assembly 60 will generate a higher luminance for visible light than for ultraviolet light. In this embodiment, it is contemplated that each individual elements from the plurality of the visible light source 48 and the plurality of ultraviolet light sources 50 generate light of the same intensity.

As should be apparent to those skilled in the art, the comparative illuminance generated by the visible light source 48 and the ultraviolet light source 50 does not need to be equal to satisfy the present invention. Moreover, the number of visible light sources 48 does not need to be equal to the number of ultraviolet light sources 50. Still further, the intensity generated the ultraviolet light sources 50 does not need to be as high as the intensity of light generated by the visible light sources 48.

For purposes of the present invention, it is contemplated that the intensity of the light generated collectively by the visible light sources 48 will be about three to four times greater than the intensity of the light generated collectively by the ultraviolet light sources 50. As such, assuming that all of the light sources 48, 50 generate approximately the same intensity of light, it is contemplated that the lighting assemblies 22, 24, 26 will include 3 to 4 times the number of visible light sources 48 compared with the number of ultraviolet light sources 50. For purposes of the present invention, the ratio of the number of visible light sources 48 to the number of ultraviolet light sources 50 is contemplated to be 1:4, 1:3, 1:2, and 1:1. Similarly, the ratio of the intensity of visible light generated by the visible light sources 48 to the intensity of ultraviolet light generated by the ultraviolet light sources follows the same guidelines of 1:5, 1:4, 1:3, 1:2, and 1:1.

Since the present invention relies on the application of ultraviolet light to the surfaces of the interior of the aircraft cabin 10 to disinfect those surfaces by killing micro-organisms on those surfaces, it is contemplated that the intensity of the ultraviolet light may not necessarily be as high as that of the visible light. Instead, it is contemplated that the duration of application of the ultraviolet light to the surfaces may be adequate to disinfect those surfaces. The controller 34 is contemplated to take this variable into account, together with other variables as should be apparent to those skilled in the art.

The controller 34 is operatively connected to the lighting assemblies 22, 24, 26 via the communication lines 36. The controller 34 controls the operation of the lighting assemblies 22, 24, 26 so that they operate in the first mode of operation where visible light is generated or in the second mode of operation where ultraviolet light is generated. As such, the controller 34 activates and/or deactivates the visible light sources 48 and the ultraviolet light sources 50 according to a control scheme, the details of which are described in greater detail below.

As should be apparent to those skilled in the art, while living organisms, such as humans, may be exposed to ultraviolet light for short periods of time without any ill effects, it is preferred to limit the exposure of living organisms to ultraviolet light. As such, the lighting system of the present invention is contemplated to include a number of interlocks to prevent activation of the second mode of operation when passengers are present within the aircraft cabin 10.

As discussed above, the controller 34 is connected to a first sensor 44 and to a second sensor 46. The controller 34 also is connected to a management system 42, which includes, but is not limited to a cabin management system and/or a flight management system.

A cabin management system refers generally to a system that controls aspects of the cabin, such as the lighting within the aircraft cabin 10, the temperature within the aircraft cabin 10, and any music and videos played in the aircraft cabin 10.

A flight management system is a system that controls and/or is cooperates with the flight parameters for the aircraft. The flight management system receives data from various components on the aircraft and provides the data to a central computer that assists with control of the aircraft.

The first sensor 44 is contemplated to provide an indication if the main passenger door to the aircraft is opened or closed. If the door is opened, the controller 34 will receive a "door opened" signal. The "door opened" signal will trigger an interlock that causes the controller 34 to disable the second mode of operation of the lighting assemblies 22, 24, 26. Only if the controller 34 receives a signal that the door is closed (e.g., a "door closed" signal) from the first sensor 44 will the controller 34 permit the lighting assembly 22, 24, 26 to operate in the second mode of operation.

As should be apparent to those skilled in the art, a "door opened" signal and a "door closed" signal may be provided in any manner consistent with the operation of the controller 34 and the program executed thereby. The present invention, therefore, does not require specifically a "door opened" signal or a "door closed" signal. Any alternatives are also encompassed by the present invention.

As should be apparent to those skilled in the art, more than one first sensor 44 may be provided on the aircraft. Naturally, if the aircraft includes several doors, a first sensor 44 is contemplated to be provided for each door. Only if all of the doors are closed will the controller 34 issue commands to the lighting assemblies 22, 24, 26 to operate in the second mode of operation.

The second sensor 46 connected to the controller 34 is contemplated to generate a signal indicating if one or more persons is present within the aircraft cabin 10. The second sensor 46 may be an infrared sensor, a motion sensor, or the like. The second sensor 46 detects the presence or the absence of a person in the aircraft cabin 10. Only if the sensor 46 generates a signal indicating the absence of a person from the aircraft cabin 10 (e.g., "cabin empty") will the controller issue commands to permit the lighting assemblies 22, 24 26 to operate in the second mode of operation. If a person is detected within the aircraft cabin 10, the controller 34 may receive a "cabin occupied" signal. If the controller receives a "cabin occupied" signal, the controller 34 will prevent the lighting assemblies 22, 24, 26 from operating in the second mode of operation.

As before, the "cabin empty" and "cabin occupied" signals are merely representative of the types of signals that may be provided to the controller from the second sensor 46. The present invention, therefore, is not limited solely to these signals.

As discussed above, the controller also is connected to a management system 42, which may be a cabin management system, a flight management system, or both.

The cabin management system is contemplated to receive input(s) from the cabin crew to indicate if the lighting assemblies 22, 24, 26 are to be operated in the first mode of operation or the second mode of operation. The cabin system also may be configured to initiate the second mode of operation at a particular time of day, a particular day of the week, or a particular day of the month, depending upon the frequency selected for disinfecting the interior of the aircraft cabin 10. For example, a crew member might schedule a two-hour duration for the second mode of operation from 3:00 to 5:00 A.M. on a particular day.

In connection with the second mode of operation, it is contemplated that the crew may be able to select a degree of disinfection for a particular instance of the operation of the second mode of operation. For example, if the crew believes that the aircraft cabin 10 might benefit from a greater level of disinfection, the crew may be able to select a longer cycle duration for the second mode of operation. Still further, the crew may be able to select a higher intensity of light generated by the ultraviolet light sources 50 to effectuate a higher level of sterilization within the aircraft cabin 10. And, it is contemplated that the crew may be able to control sterilization in areas of the aircraft cabin 10. For example, the crew may be able to select a higher degree of sterilization for the lavatory and the galley than for the seats 14 within the aircraft cabin 10.

The flight management system on the aircraft provides flight information to the flight deck and to the control systems on board the aircraft. The flight management system may be configured to provide any number of different inputs to the controller 34. For example, if the flight management system generates a signal indicating that the aircraft is in operation, the controller 34 will prevent operation of the lighting assemblies 22, 24, 26 in the second mode of operation. Still further, the flight management system may indicate if the aircraft is parked. If the aircraft is parked, the controller 34 will permit the lighting assemblies 22, 24, 26 to operate in the second mode of operation.

As illustrated in FIG. 2, and as discussed above, the controller 34 is contemplated to be connected to the window shades 40. It is contemplated that the controller 34 may be configured to generate a signal to close the window shades 40 before initiating the second mode of operation of the lighting assemblies 22, 24, 26. This operation is considered to be optional, because the aircraft, when parked on a runway, may be at a location where it may not be necessary to close the window shades 40 before initiating the second mode of operation.

Still further, the controller 34 is contemplated to be connected to the seats 14. If so, the controller 34 may reconfigure the seats 14 before initiating the second mode of operation. Here, it is contemplated that the controller 34 may place the seats 14 in a configuration to maximize exposure of the surfaces of the seats 14 to the ultraviolet light, thereby assisting with the disinfecting of the various surfaces within the aircraft cabin 10. Still further, the control 34 may issue signals to the seats 14 to place the seats 14 into various configurations during a disinfection cycle. For example, the seats 14 may start in the TTL configuration, as indicated by the seat 14a. Before completing of the disinfection cycle, the seats 14 may be reconfigured to the recline position, as indicated with respect to the seat 14b. As should be apparent, the controller 34 is contemplated to issue instructions to the seats 14 so that the seats 14 are bathed in the ultraviolet light when the lighting assemblies 22, 24, 26 operate in the second mode of operation.

Figure 7:
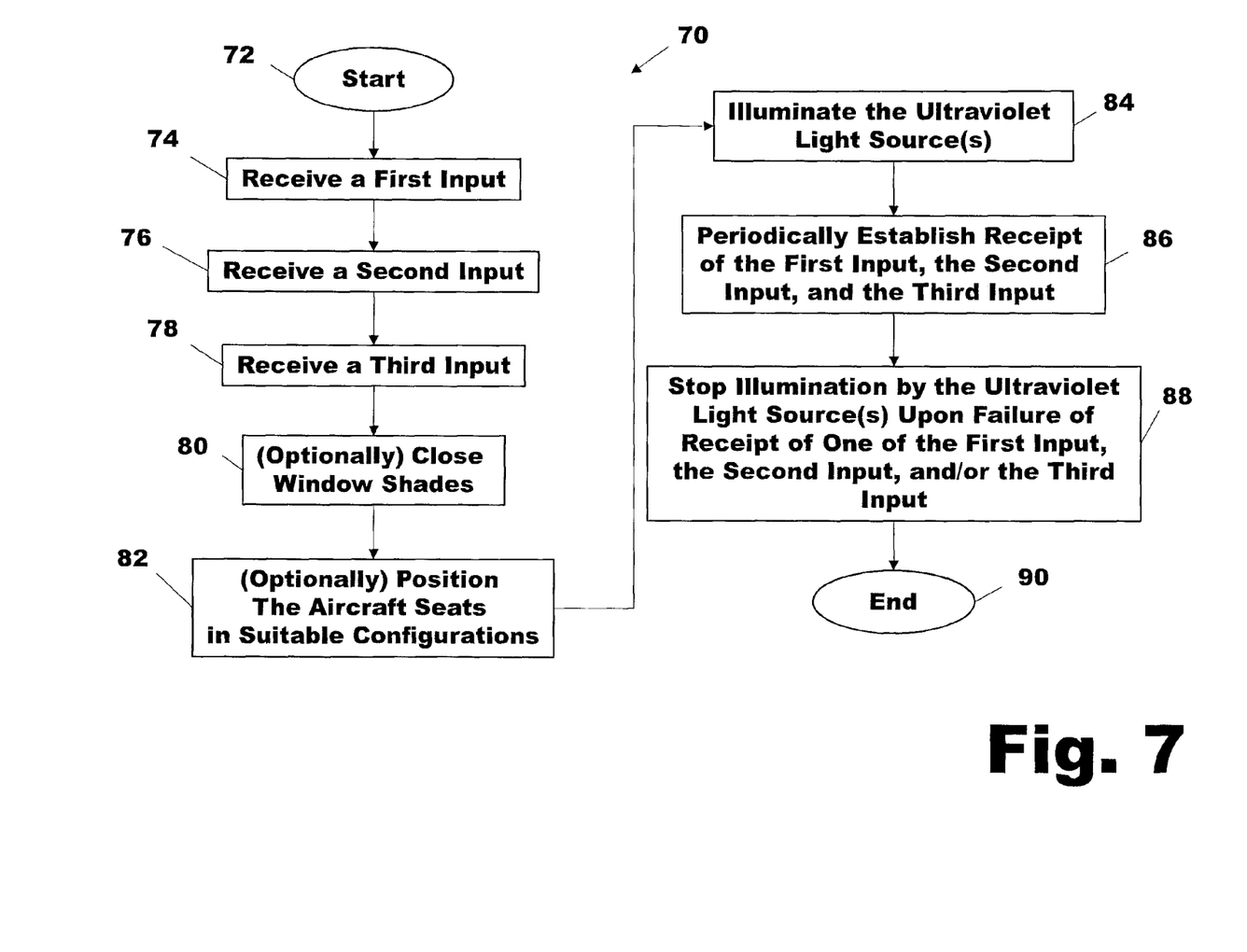
FIG. 7 is a flow chart illustrating one contemplated method for disinfecting a vehicle cabin according to the present invention.

FIG. 7 is a flow chart that illustrates one contemplated method 70 of operation of the lighting assemblies 22, 24, 26 that are discussed above. While the method is described in terms of "steps," the discussion of the operations as a "step" should not be understood to limit the scope of the present invention. One or more of the steps may be combined or may be parsed into a plurality of steps without departing from the scope of the present invention. In addition, the steps need not be performed in the order illustrated. It is contemplated that one or more of the steps may be performed in an order differing from the arrangement provided in FIG. 7 without departing from the present invention.

With reference to FIG. 7, the method 70 starts at step 72.

At step 74, the controller 34 receives a first input. The first input is contemplated to be received from the first sensor 44. As discussed above, the first sensor 44 is contemplated to be a sensor that detects if a door to the aircraft is opened or closed. For this step, the first input is contemplated to be a "door closed" signal (or its equivalent). The "door closed" signal is contemplated to release a first interlock within the controller 34. As such, if the remaining interlocks also are released, the controller will initiate operation of the lighting assemblies 22, 24, 26 in the second mode of operation, where ultraviolet light is provided in the aircraft cabin 10 to disinfect/sterilize various surfaces within the aircraft cabin 10.

At step 76, the controller 34 receives a second input. The second input is contemplated to be generated by the second sensor 46. As discussed above, the second sensor 46 is contemplated to provide an indication of the presence or absence of a person within the aircraft cabin 10. If the second sensor 46 sends a signal to the controller 34 that indicates the aircraft cabin 10 is empty, the controller 34 may release a second interlock to permit the second mode of operation.

At step 78, the controller 34 receives a third input. The third input is contemplated to be provided by the management system 42. As discussed above, this third input may be a signal generated by the flight management system indicating that the aircraft is parked. If an "aircraft parked" signal is received (or its equivalent), the controller 34 is contemplated to be configured to release a third interlock to permit the lighting assemblies 22, 24, 26 to operate in the second mode of operation.

Separately, the management system 42 may be a cabin management system, which might require input from a crew member before initiating the second mode of operation.

At step 80, the controller 34 issues a signal to the window shades 40 to close the window shades 40 prior to initiating the second mode of operation. As indicated above, this operation is optional.

At step 82, the controller 34 sends a signal to the aircraft seats 14 to position the seats 14 in a configuration (or configurations) to maximize coverage of the seats 14 by the ultraviolet light. This step 82 also is considered to be an optional step that may be initiated before the second mode of operation. As also discussed above, the controller 34 may be configured to reposition the seats during the second mode of operation of the lighting assemblies 22, 24, 26.

At step 84, the controller 34 sends a signal to activate the ultraviolet light generators 50 in the second mode of operation.

At step 86, it is contemplated that the controller 34 will periodically establish receipt of the first, second, and third inputs. It is contemplated that, if one or more of the first, second, and third inputs change, the controller 34 will discontinue the second mode of operation. For example, if the second sensor 46 were to detect the presence of a person in the aircraft cabin 10 during a sterilization cycle, the controller 34 is contemplated to cease the second mode of operation.

In connection with step 86, the controller 34 may establish receipt of the first input, the second input, and the third input every second, group of seconds, minute, group of minutes, hour, group of hours, etc., as required or as desired. Since exposure of a person to ultraviolet light should be minimized, it is contemplated that the controller 34 will establish receipt of the three inputs at least every few seconds or so. As should be apparent, the cycle time may be programmed into the controller 34. Alternatively, the controller 34 may be configured to receive, from a crew member, the cycle time for step 86.

At step 88, the controller 34 ceases illumination by the ultraviolet light generators 50 upon failure of receipt of at least one of the first, second, or third inputs.

The method 70 stops at step 90.

In connection with the method 70, it is contemplated that the controller 34 will receive all three of the first input, the second input, and the third input. As should be apparent to those skilled in the art, at least one input is anticipated to be needed to ensure an acceptable operation of the light assemblies 22, 24, 26. Alternatively, more than three inputs may be required, as also should be apparent to those skilled in the art.

As noted above, the embodiment(s) described herein are intended to be exemplary of the wide breadth of the present invention. Variations and equivalents of the described embodiment(s) are intended to be encompassed by the present invention, as if described herein.

What is claimed is:

1. A lighting assembly for an aircraft, comprising:
a visible light source generating visible light;
an ultraviolet light source generating ultraviolet light; and
a controller connected to the lighting assembly to control
operation of the visible light source and the ultraviolet
light source;

wherein the visible light source is disposed adjacent to the ultraviolet light source, wherein the visible light source illuminates a first illumination area with the visible light when the lighting assembly operates in a first operation mode, wherein the ultraviolet light source illuminates a second illumination area with the ultraviolet light when the lighting assembly operates in a second mode of operation, wherein the first illumination area substantially overlaps the second illumination area; and wherein the controller is connected to a plurality of window shades and closes the window shades when the ultraviolet light source operates in the second mode of operation.

2. The lighting assembly of claim 1, wherein the visible light source and the ultraviolet light source are disposed on a single substrate.

3. The lighting assembly of claim 2, wherein the visible light source comprises a plurality of visible light generators.

4. The lighting assembly of claim 3, wherein the plurality of visible light generators comprise LEDs.

5. The lighting assembly of claim 3, wherein the ultraviolet light source comprises a plurality of ultraviolet light generators.

6. The lighting assembly of claim 5, wherein the plurality of ultraviolet light generators comprise LEDs.

7. The lighting assembly of claim 5, wherein a first number of the plurality of visible light generators is greater than or equal to a second number of the plurality of ultraviolet light generators.

8. The lighting assembly of claim 1, further comprising:
a first sensor connected to the controller to detect when a door to the aircraft is closed and generate a first input signal for the controller.

9. The lighting assembly of claim 1, further comprising a second sensor to detect the absence of a person in the aircraft and generate a second input for the controller.

10. The lighting assembly of claim 9, wherein the second sensor is a motion sensor.

11. The lighting assembly of claim 1, wherein the controller is operatively connected to a management system and receives a third input from the management system indicating that the aircraft is parked.

12. The lighting assembly of claim 1, wherein the controller is connected to a plurality of seats and positions the seats in a configuration so that the seats are bathed in the ultraviolet light when the ultraviolet light source operates in the second mode of operation.

13. A method of operating a lighting assembly comprising a visible light source generating visible light, an ultraviolet light source generating ultraviolet light, a controller connected to the lighting assembly to control operation of the visible light source and the ultraviolet light source, a first sensor connected to the controller to detect when a door to an aircraft is closed and generate a first input, and a second sensor to detect the absence of a person in the aircraft and generate a second input, wherein the visible light source is disposed adjacent to the ultraviolet light source, wherein the visible light source illuminates a first illumination area with the visible light when the lighting assembly operates in a first operation mode, and wherein the ultraviolet light source illuminates a second illumination area with the ultraviolet light when the lighting assembly operates in a second mode of operation, wherein the controller is operatively connected to a management system and receives a third input from the management system indicating that the aircraft is parked, and wherein the controller is connected to a plurality of window shades, the method comprising:
receiving, by the controller, the first input;
receiving, by the controller, the second input;
receiving, by the controller, the third input;
initiating the second operation mode after receipt of the first input, the second input, and the third input; and
closing, by the controller, the window shades when the ultraviolet light source operates in the second mode of operation.

14. The method of claim 13, wherein the controller is connected to a plurality of seats, the method further comprising:
positioning the seats in a configuration so that the seats are bathed in the ultraviolet light when the ultraviolet light source operates in the second mode of operation.

15. The method of claim 13, wherein the controller is connected to a plurality of seats, the method further comprising:
positioning the seats in a configuration so that the seats are bathed in the ultraviolet light when the ultraviolet light source operates in the second mode of operation.

16. The method of claim 13, further comprising:
checking periodically, by the controller, the first input, the second input, and the third input.

17. The method of claim 16, further comprising:
stopping the second operation mode upon failure of receipt of at least one of the first input, the second input, or the third input.

* * * * *